United States Patent [19]
Johnson et al.

[11] Patent Number: 5,684,106
[45] Date of Patent: Nov. 4, 1997

[54] SUPERABSORBENT POLYMERS AND PRODUCTS CONTAINING THEM

[75] Inventors: Ian Michael Johnson; Pauline Lesley Couldwell, both of West Yorkshire, United Kingdom

[73] Assignee: Allied Colloids Limited, United Kingdom

[21] Appl. No.: 464,784
[22] PCT Filed: Oct. 26, 1994
[86] PCT No.: PCT/GB94/02351
 § 371 Date: Jun. 23, 1995
 § 102(e) Date: Jun. 23, 1995
[87] PCT Pub. No.: WO95/11932
 PCT Pub. Date: May 4, 1995

[30] Foreign Application Priority Data

Oct. 27, 1993 [GB] United Kingdom .................. 9322119

[51] Int. Cl.$^6$ .......................... C08F 34/00; C08F 220/06; A61L 15/00
[52] U.S. Cl. ............................................. 526/295; 526/310
[58] Field of Search ...................................... 526/310, 295

[56] References Cited

FOREIGN PATENT DOCUMENTS

| | | |
|---|---|---|
| 0339461 | 11/1989 | European Pat. Off. . |
| 0530438 | 3/1993 | European Pat. Off. . |
| 0532002 | 3/1993 | Germany . |
| 9200108 | 1/1992 | WIPO . |
| 9415651 | 7/1994 | WIPO . |
| 9420547 | 9/1994 | WIPO . |

OTHER PUBLICATIONS

DD292642 91/08/08 Jaeger et al—abstract pp. 9–11.
DD292219 91/07/25 Wandrey et al—abstract pp. 12–13.
"Gelation in the polymerization of tetraallylammonium chloride" Matsumoto et al. Makromol Chem. Rapid Commun 10(1) 1989 abstract pp. 16–17.

Primary Examiner—Joseph L. Schofer
Assistant Examiner—N. Sarofim
Attorney, Agent, or Firm—Ostrolenk, Faber, Gerb & Soffen, LLP

[57] ABSTRACT

Particulate superabsorbent polymeric material which is a partially neutralised polymer of an ethylenically unsaturated carboxylic monomer cross linked by a triethylenic or higher ethylenic cross linking agent, preferably tetra allyl ammonium chloride, absorbs above 15 grams, and often above 18 grams, aqueous saline per gram polymeric material in 60 minutes under a load of 63,000 dynes per square centimeter. The polymer preferably has surface cross linking caused by contacting the polymer particles with inorganic and/or covalent cross linking agent for the polymer.

21 Claims, No Drawings

SUPERABSORBENT POLYMERS AND PRODUCTS CONTAINING THEM

BACKGROUND OF THE INVENTION

It is standard practice to provide superabsorbent polymeric material in the form of particles wherein the polymer has been obtained by copolymerization of monoethylenically unsaturated carboxylic monomer and polyethylenically unsaturated cross linking agent. The carboxylic monomer groups are usually at least partially neutralized, for instance at least 50% molar in the form of sodium salt.

In EP-A-339461, it is proposed to provide such superabsorbent material which can absorb at least 27 ml of aqueous saline (as hereinafter defined) per gram of superabsorbent material while under a restraining pressure of at least 21,000 dynes per square centimeter. Aqueous saline herein is to be understood as being an aqueous solution of sodium chloride containing 0.9 weight % sodium chloride and all absorbency values refer to the absorption of this.

EP 339461 does not describe how those polymers are to be made and does show that the absorption value tends to drop significantly as the load increases. For instance the absorption at 58,600 dynes per square centimeter in one example is 8 g/g compared to a value of 26 g/g at 20,700 dynes/cm$^2$.

In EP 532002, it is proposed to test the absorption under a load provided by a 200 gram weight.

Although these absorption under load tests do give an indication of the ability of the superabsorbent material to absorb urine while under load, such tests indicate only one of several parameters that can be examined.

Another parameter is the centrifuge retention capacity, which indicates the volume of liquid that the superabsorbent will hold on to under applied pressure. About 200 mg of superabsorbent is sealed in a tea-bag of approx. size 6.35 cm×7.62 cm (2.5 inches×3 inches) and immersed in 0.9% sodium chloride solution for 30 mins. The tea-bag is removed and placed in a basket centrifuge for 3 mins. at 1600 rpm (centrifugal force approx. 250G). A tea-bag without polymer is used as the blank.

$$\text{Centrifuge retention capacity} = \frac{\text{wt. of wet polymer} - \text{blank}}{\text{wt. of dry polymer}}$$

Generally for commercial superabsorbents, this value is at least 28 g/g of 0.9 weight % sodium chloride solution.

Another parameter is the rewet parameter, which gives an indication of the performance of the polymer when combined with a fiber matrix in a diaper type construction.

Ideally, a superabsorbent material would give optimum properties in all these tests, but we have found that known polymers that satisfy the "absorption under load" (AUL) test of EP 339461 frequently give poor rewet test results.

It would therefore be desirable to be able to provide superabsorbent particulate polymeric material that gives better performance in use and, in particular, such material which complies with a parameter that is a better indication of overall performance properties.

SUMMARY OF THE INVENTION

According to the invention, we now provide a superabsorbent polymeric material which is in the form of particles, wherein the polymeric material has been obtained by copolymerization of monoethylenically unsaturated carboxylic monomer and a polyethylenically unsaturated cross linking agent having at least three ethylenically unsaturated bonds, the carboxylic groups in the polymer have been at least partially neutralized, and the particulate material absorbs above 15 grams synthetic urine (i.e., aqueous saline as defined above) per gram polymeric material in 60 minutes under a load of 63,000 dynes per square centimeter.

DETAILED DESCRIPTION OF THE PREFERRED EMBODIMENTS

In order that the superabsorbent material has good performance properties in use, these improved "absorption under high load" values should be accompanied by conventional, commercially suitable, centrifuge retention capacity values of at least about 28 g/g and often in the range 29 or 30 up to, for instance, 33 or 34 or in some instances higher, such as up to 36 or more.

In order to obtain the improved absorption under load characteristics while maintaining conventional commercial centrifuge retention capacity, it is necessary to optimize the processes of making the particulate superabsorbent material in order to obtain the desired properties. Since there are several variables involved in the production of superabsorbent particles (including initiation conditions, monomer concentration, choice and amount of cross linking agent and surface cross linking), there are several variables that can be adjusted in order to obtain the required properties. We have found that particularly useful results are obtained by appropriate selection of cross linking agent, often accompanied by appropriate selection of conditions for surface cross linking.

In this specification, the units and methods of measuring the load are broadly as described in EP 339461, and in particular the load of 63,000 dynes per square centimeter is obtained by applying a weight of 300 grams over a circular surface area of 2.54cm (1 inch) diameter, i.e., as described on page 7 of EP-A-339461 except that a weight of 300 grams is used instead of 100 grams. In other units, the load is 6 kilo pascals or 0.9 psi.

We also mention herein loads of 21,000 dynes per square centimeter (100grams over 2.54cm, 0.3 psi and 2 kilo pascal) and loads of 42,000 dynes per square centimeter (200 grams over 2.54 cm, 4 kilo pascal and 0.6 psi).

The preferred material absorbs at least 16 and preferably at least 17 grams per gram in 60 minutes under a load of 63,000 dynes per square centimeter. In general, values in the range 18 to 28, preferably 20 to 25, g/g in 60 minutes are preferred.

We find surprisingly that polymers that are made to meet this absorbency parameter, and optionally other absorbency parameters described below, give much better performance on other tests such as the rewet test and are, in practice, more effective as superabsorbents for use in diapers and other absorbent articles.

The polymers preferably have an absorbency value at a load of 42,000 dynes per square centimeter of at least 18 or 20 and generally at least 22 grams synthetic urine in 60 minutes under this load. Preferred polymers absorb 20 to 28 or 30, generally 20 to 25, grams per gram in 60 minutes under this load.

Another useful parameter is the amount of absorption in 10 minutes. Under a load of 21,000 dynes per square centimeter, it is preferred that the polymer absorbs at least 15 and preferably at least 20, for instance 18 to 28, grams synthetic urine per gram polymer in 10 minutes. Under a load of 42,000 dynes per square centimeter, it is preferred that the polymer absorbs at least 10 and preferably at least 15, for instance 13 to 25 g/g in 10 minutes. Under a load of 63,000 dynes per square centimeter, it is preferred that the polymer absorbs at least 8 and preferably at least 12, for instance 10 to 20, grams per gram in 10 minutes.

Surprisingly, the absorbency in 60 minutes under a load of 21,000 dynes per square centimeter (i.e., the value in the test described in EP-A-339461 ) does not seem particularly critical. Although useful polymers for use in the invention can have the absorbency of at least 27 g/g at 21 dynes per square centimeter proposed in EP 339461, it is also possible in the invention to obtain excellent results under higher loads, and excellent performance in practice, even though the absorbency over 60 minutes at 21,000 dynes per square centimeter is below 27 g/g, for instance it may be in the range 20 to 26 g/g.

The polymer is made by copolymerization of monoethylenically unsaturated carboxylic monomer with polyethylenically unsaturated cross linking agent. Polymerization processes of this general type are well known in the literature for making superabsorbent polymers but conventional techniques have not produced the polymers now being defined. For instance, a conventional polymerization comprises aqueous polymerization of partially neutralized acrylic acid in the presence of a difunctional cross linking agent such as methylene bis acrylamide. This gives inadequate properties, according to our new tests, and the properties are inadequate even when the resultant particles are subjected to surface cross linking by one of the generally known techniques.

A wide range of cross linking agents have been proposed in the literature including various tri-functional and tetra-functional and higher functional cross linkers. Usually the tri-functional and tetra-functional cross linking agents have no more than two ethylenically unsaturated bonds substituted on to a single atom. For instance tetra-allyl butane diamine is mentioned as an example in WO91/18031 and this has two allyl groups substituted on to one amino nitrogen atom and two allyl groups substituted on to another amino nitrogen atom. The same disclosure also mentions, for instance, triallylamine, wherein all three allyl groups are substituted on to the same amino nitrogen atom. Blends of triallylamine with methylene bis acrylamide or other cross linkers are also exemplified.

In the invention, we find that it is important that at least half, and preferably substantially all, the cross linking agent used in the copolymerization is provided by a material which has at least three ethylenically unsaturated bonds, preferably substituted on to a single atom. For instance, it may have at least three allyl or other ethylenically unsaturated groups substituted on to a single atom, usually an amino nitrogen atom. We believe that this close proximity of the ethylenic unsaturation contributes to the formation of a gel structure in the polymer that An turn contributes to the defined absorption properties. Preferably at least half of the polyethylenically unsaturated cross linking agent has at least four of the ethylenically unsaturated bonds, preferably on to a single atom. Thus preferred cross linkers are triallylamine and, especially, tetra-allyl ammonium compounds.

Although the copolymerization can be conducted on the free acid monomer followed by partial or complete neutralization, it is preferred that the polymerization is conducted on partially neutralized monomer or even wholly neutralized monomer, e.g., acrylic acid-sodium acrylate blends. Since it is preferred that the cross linking agent should be soluble in the aqueous polymerization medium the polyethylenically unsaturated cross linking agent should be water soluble, and it is therefore preferred that the cross linking agent should be an acid addition (e.g., triallylamine hydrochloride) or quaternary ammonium salt.

The preferred cross linkers are quaternary ammonium salts of triallylamine, for instance the metho sulphate, methyl chloride, methyl bromide or methyl iodide salt of triallylamine or, preferably, the allyl chloride or other allyl quaternary salt of triallylamine. The preferred cross linker is tetra-allyl ammonium chloride. Although it can be used in combination with other cross linkers, such as triallyl ammonium metho sulfate, preferably it is used as the only cross linker.

The amount of cross linker may be selected within the conventional range, for instance 0.05 to 3%, often around 1 or 1.5%.

The monoethylenically unsaturated carboxylic monomer is generally acrylic acid but can be any of the other conventional carboxylic monomers. It can be copolymerized with other water soluble monomers but generally the polymer is a homopolymer of acrylic acid. The degree of neutralization of the carboxylic groups during polymerization or in the final polymer (for instance as a result of treating the polymer with sodium hydroxide or other alkali) is usually at least 50% and generally at least 70%. It is generally unnecessary for it to be above 90%.

The polymerization should be initiated using an initiator system that will contribute to the formation of the desired gel properties. This can involve a thermal system or a redox system or a mixture, but we find satisfactory results are obtained by use of a combination of a reducing agent such as sodium sulfite with an oxidizing agent such as a peroxy compound, especially tertiary butyl hydrogen peroxide.

The polymerization is generally conducted on aqueous monomer solution having a monomer content in the range 25 to 60%, generally 25 to 40%, often around 25 to 35%.

The polymerization can be conducted as a reverse phase bead polymerization in a water immiscible liquid in known manner, to give an appropriate particle size, or the resultant particles may be comminuted. Preferably, however, the polymerization is conducted as a bulk gel polymerization and is followed by comminution and drying in conventional manner.

The particle size is generally above 100 microns and below 1 mm. Preferably it is above about 200 or 300 µm. Preferably it is not more than about 600 or 700 µm. A range of 300 to 600 µm is suitable.

It is generally preferred to subject the particles to a surface cross linking treatment, as a result of which the cross linking density in the surface of the particles is greater than in the central parts of the particles. Techniques of surface cross linking preformed superabsorbent particles are known in the literature and, when the particles are being made by reverse phase polymerization, it is also known to be able to surface cross link them during their formation or prior to recovery from the reverse phase system.

The surface cross linking may be brought about by contact of the surfaces with an inorganic cross linking agent, for instance aluminium sulfate, sodium aluminate or other polyvalent metal compound.

Preferably, however, some or all of the cross linking is by reaction with a material that reacts covalently with the polymer, for instance a silane coupling agent (for instance as described in EP 195406) or a glycidyl ether or other epoxy or other material capable of reacting with the carboxylic groups in the polymer. For disclosures of surface cross linking mechanisms reference may be made to, for instance, EP 317106, 503268, 386897, U.S. Pat. No. 5,053,460 and U.S. Pat. No. 4,587,308.

The surface cross linking effect may be supplemented by treating the surface with finely divided silica such as Aerosil or Sipernat (trade marks). Typically this is applied as a slurry. For instance, the particles may be contacted with an aqueous composition containing not more than 10 or 15% of finely divided silica. If desired, the particles may be treated sequentially by aqueous inorganic cross linking agent, aqueous organic cross linking agent and aqueous silica, in any order, or two or more of them may be applied in a single coating composition.

The surface cross linking can be achieved merely by, for instance, spraying the particles, generally while entrained in air, with a dilute solution of a cross linking agent, wherein the solution preferably contains both a covalent cross linking agent and silica. However any other convenient method of contacting the particles with the surface cross linking agents can be used. Often the treated particles are then heat treated for instance to a temperature of 50° to 200° C., e.g., 80° to 120° C., for five minutes to an hour or whatever time is appropriate for optimum results.

In order to promote the surface cross linking in such a way as to maximise the "absorption under high load" value in accordance with the invention, it can be desirable to take steps to control the penetration of the surface cross linking agent into the structure of the particulate material. To control penetration, it can be desirable to adjust the concentration of the cross linking agent in a dilute aqueous solution that is used for the contact. Preferably the surface cross linking is performed by contacting the particles with an aqueous solution containing less than 25% cross linking agent, preferably less than 10% cross linking agent, for instance 1 to 10%. It may contain less than 5% cross linking agent, for instance 0.5 to 5%.

It can be desirable to provide both ionic and covalent cross linking. The particles may be contacted sequentially with aqueous solutions of covalent and ionic cross linking agents or they may be contacted with a single solution containing both cross linking agents dissolved in it.

The amount of cross linker solution that is applied is generally such that the particles absorb 0.01 to 2% of each cross linker, generally 0.1 to 1%, often greater than 0.2 or 0.5%, of total cross linker.

Although satisfactory results are generally obtained merely by surface cross linking the individual particles, good results can also be obtained by agglomerating the particles wherein the agglomeration is caused by contacting the superabsorbent particles with the aqueous cross linking agent (generally including silica) under conditions that the particles agglomerate, followed by drying the agglomerates.

If desired, the agglomerates may be subjected to comminution to reduce them to the desired final particle size.

By appropriate selection of the polymerisable monomer or monomers, the cross linking agent or cross linking agents, the initiator and other polymerization conditions, the particle size, optional surface cross linking (including selection of the epoxy or other cross linking agent and usually silica) and optional agglomeration with a cross linking agent, it is easily possible to obtain novel polymers having the defined parameters.

Best results are obtained by polymerizing partially neutralized acrylic acid using tetra-allyl ammonium chloride as cross linker and a redox system such as sulfite-peroxide, followed by surface cross linking using a dilute aqueous solution of a glycidyl ether or other covalent cross linking agent, preferably in combination with finely divided silica and/or a dilute aqueous solution of aluminium salt.

The following is an example of a preferred synthesis of the novel polymer:

EXAMPLE 1

221 g of 46% aqueous sodium hydroxide is added to 244 g glacial acrylic acid and 435 g distilled water to form 1,000 g of a 75% neutralized 30% solids sodium acrylate solution. This is de-oxygenated with nitrogen. 2 mls of a 60% w/v aqueous solution of ethylene diamine tetra-acetic acid is then added followed by 3.3 mls of a 45% w/v aqueous solution of tetra-allyl ammonium chloride.

Polymerization is then initiated by the addition of 0.9 mls of 0.5% w/v aqueous solution of sodium sulfite followed by 0.45 mls of a 0.5% w/v aqueous solution of tertiary butyl hydrogen peroxide.

Polymerization is allowed to go to completion. The resultant gel is then comminuted and dried in an oven and ground to the selected particle size, typically such that as much as possible is between 300 and 600 μm.

A dispersion is formed of 7.5% ethylene glycol diglycidyl ether and 7.5% finely divided silica and 85% by water. This is sprayed on to the particles to give a dry pick-up of 1% of each cross linking agent, based on the weight of the particles. The particles are then redried.

The particles obtained after the surface cross linking are described as product A.

In another test, the process is repeated using triallyl methyl ammonium metho sulfate as the cross linking agent and D is the polymer obtained using triallyl methyl ammonium metho sulfate as the cross linking agent with surface cross linking as in the example.

The centrifuge retention capacity (CRC) and absorbency under load after 60 minutes at loads of 100, 200 and 300 g are recorded for products A and D and for products E to K as shown in the following table:

| | Absorbency under load | | | |
|---|---|---|---|---|
| Sample | 100 g | 200 g | 300 g | CRC |
| A | 27 | 22 | 16 | 34 |
| D | 26 | 19 | 15 | 31 |
| E | 29 | 10 | 8 | 33 |
| F | 23 | 13 | 7 | 30 |
| G | 21 | 9 | 9 | 31 |
| I | — | — | 11 | 29 |
| J | — | — | 10 | 28 |
| K | — | — | 8 | 29 |

E, F and G are commercially available superabsorbent polymers. I, J and K are polymers obtained used methylene bis acrylamide as the cross linking agent in various amounts but without surface cross linking. When methylene bis acrylamide is used with surface cross linking, the values are lifted by only a small amount.

The clear benefit of the polymers defined in the invention (A and D, and preferably the tetra-allyl, surface cross linked polymer A) is apparent.

EXAMPLE 2

A process broadly as described in Example 1 for the production of product D is conducted except that the cross linker is about 0.6% (based on monomer) tetra allyl ammonium chloride, the initiator is a ferric salt, ascorbic acid, hydrogen peroxide, sodium persulfate initiator and the final particles were each coated with 3% solutions of ethylene glycol diglycidyl ether, aluminium sulfate and Sipernat 22S silica to give a pick-up of 0.4% of each. The resultant product had CRC 32 g/g, and absorption under load values of 28 and 20 g/g at loads of 100 and 300 g respectively.

The novel polymers are preferably incorporated into absorbent structures such as diapers, sanitary pads, tissues and other fibrous materials, in conventional manner, for instance as described in EP-A-339461. These absorbent materials may be incorporated into diapers including topsheet, backsheet and appropriate fastenings, all in conventional manner.

It is not possible to define a standardized rewet test since even quite small differences in the details of the absorbent structure in which the superabsorbent particles are incorporated will tend to give slightly different values. However, provided the same absorbent structure is used, comparative rewet tests are valuable.

In our rewet tests, 5 g of polymer are scattered between two layers of fluff and the rewet values are then compared under different loadings, being subjected to first, second and third rewets in conventional manner. Product A and a commercial product were tested by this test and the results are set out in Table 2 below.

TABLE 2

|  | test | 1st | 2nd | 3rd |
| --- | --- | --- | --- | --- |
| Product A | absorption time (secs) | 32 | 36 | 60 |
| 5 kilo wt. | rewet mls. | 0.4 | 6.8 | 7.7 |
| Product A | absorption time (secs) | 32 | 48 | 62 |
| 10 kilo wt. | rewet mls. | 2.6 | 6.8 | 11.5 |
| Commercial product | absorption time (secs) | 34 | 65 | 80 |
| 5 kilo wt. | rewet mls. | 1.7 | 6.3 | 11.8 |
| Commercial product | absorption time (secs) | 35 | 72 | 103 |
| 10 kilo wt. | rewet mls. | 4.5 | 8.2 | 14.2 |

The clear benefit of product A, compared to the commercial product, is apparent from these values. The rewet value should be as low as possible as should the absorption time. The invention also includes polymers in fiber form and polymers having the specified absorption values which can be cross linked graft polymers. Preferably all the polymers of the invention have a low content of extractables.

We claim:

1. A superabsorbent polymeric material which is in the form of particles, wherein the polymeric material has been obtained by copolymerization of an aqueous mixture of monomers consisting essentially of partially or wholly neutralized acrylic acid and a polyethylenically unsaturated cross linking agent having at least three ethylenically unsaturated bonds which is tetra allyl ammonium chloride, bromide or iodide, and which is soluble in the aqueous mixture; and the particulate material absorbs above 15 grams aqueous saline per gram polymeric material in 60 minutes under a load of 63,000 dynes per square centimeter.

2. A polymeric material according to claim 1 in which the particles have been provided with surface cross linking by contacting the particles with an aqueous composition containing not more than 25% by weight of cross linking agent selected from inorganic cross linking agents and cross linking agents that react covalently with carboxylic groups in the polymer and heat treating the particles at a temperature of 50° to 120° C.

3. A polymeric material according to claim 2 having a centrifuge retention capacity of at least 28 grams aqueous saline per gram polymeric material.

4. A polymeric material according to claim 2 which absorbs at least 17 grams aqueous saline per gram polymeric material in 60 minutes under a load of 63,000 dynes per square centimeter.

5. A polymeric material according to claim 2 which absorbs at least 18 to 28 grams aqueous saline per gram polymeric material in 60 minutes under a load of 63,000 dynes per square centimeter.

6. A polymeric material according to claim 2 which absorbs at least 20 to 25 grams aqueous saline per gram polymeric material in 60 minutes under a load of 63,000 dynes per square centimeter.

7. A polymeric material according to claim 2 in which the polyethylenic cross linking agent is tetra allyl ammonium chloride, bromide or iodide.

8. A polymeric material according to claim 2 in which the aqueous composition contains not more than 10% by weight of the cross linking agent.

9. A composition according to claim 2 in which the aqueous composition contains glycidyl ether as the cross linking agent.

10. A composition according to claim 2 in which the aqueous composition also contains silica.

11. A composition according to claim 2 in which the aqueous composition contains ethylene glycol diglycidyl ether and silica.

12. An absorbent structure which is a diaper, sanitary pad or tissue incorporating absorbent polymeric material according to claim 1.

13. A polymeric material according to claim 1 in which the particles additionally have surface cross-linking caused by reaction between the surface of the particles and cross-linking agent selected from inorganic cross-linking agents and cross-linking agents that react covalently with the carboxylic groups in the polymer.

14. A superabsorbent polymeric material which is in the form of particles, wherein the polymeric material has been obtained by copolymerization of an aqueous mixture of monomers consisting essentially of partially or wholly neutralized acrylic acid and a polyethylenically unsaturated cross linking agent having at least three ethylenically unsaturated bonds which is tetra allyl ammonium chloride, bromide or iodide, and which is soluble in the aqueous mixture, and the particulate material absorbs above 15 grams aqueous saline per gram polymeric material in 60 minutes under a load of 63,000 dynes per square centimeter.

15. A superabsorbent polymeric material which is in the form of particles which absorb above 15 grams aqueous saline per gram polymeric material in 60 minutes under a load of 63,000 dynes per square centimeter product of the process comprising copolymerizing an aqueous mixture of monomers consisting essentially of partially or wholly neutralized acrylic acid and a polyethylenically unsaturated cross-linking agent selected from tetra allyl ammonium chloride, tetra allyl ammonium bromide and tetra allyl ammonium iodide, and which is soluble in the aqueous mixture.

16. A polymeric material according to claim 15 in which the process comprises the additional step of contacting the particles with an aqueous composition containing not more than 25% by weight of cross-linking agent selected from inorganic cross-linking agents and cross-linking agents that react covalently with carboxylic groups and the polymer and heat treating the particles at a temperature of 50° to 120° C.

17. A polymeric material according to claim 1 in which the polyethylenic cross-linking agent is tetra allyl ammonium chloride.

18. A polymeric material according to claim 13 in which the polyethylenic cross-linking agent is tetra allyl ammonium chloride.

19. A polymeric material according to claim 15 in which the polyethylenic cross-linking agent is tetra allyl ammonium chloride.

20. A particulate superabsorbent polymer material copolymerization product of monomers consisting essentially of partially or wholly neutralized acrylic acid and tetra allyl ammonium chloride, bromide or iodide which absorbs about 15 grams aqueous saline per gram in 60 minutes under a load of 63,000 dynes per square centimeter.

21. A polymeric material according to claim 20 which is the copolymerisation product of at least partly neutralized polyacrylic acid and tetra allyl ammonium chloride and absorbes at least 18 to 28 grams of aqueous saline.

* * * * *